United States Patent [19]
Halperin et al.

[11] Patent Number: 5,633,274
[45] Date of Patent: May 27, 1997

[54] CANCER TREATMENTS

[75] Inventors: Jose Halperin, Brookline; Carlo Brugnara, Newton Highlands, both of Mass.

[73] Assignee: President and Fellows of Harvard College, Cambridge, Mass.

[21] Appl. No.: 18,828

[22] Filed: Feb. 18, 1993

[51] Int. Cl.$^6$ .................................................. A61K 31/415
[52] U.S. Cl. ........................ 514/405; 514/385; 514/396
[58] Field of Search ................................. 514/396, 405, 514/385

[56] References Cited

U.S. PATENT DOCUMENTS

| | | | |
|---|---|---|---|
| 3,678,030 | 7/1972 | Yamazaki et al. | 260/211.5 R |
| 3,901,908 | 8/1975 | Fitzi et al. | 260/309 |
| 3,940,486 | 2/1976 | Fitzi | 424/263 |
| 3,965,112 | 6/1976 | White et al. | 260/309 |
| 4,073,922 | 2/1978 | Wyburn-Mason | 424/273 R |
| 4,119,723 | 10/1978 | Wyburn-Mason | 424/273 R |
| 4,218,449 | 8/1980 | Wyburn-Mason | 424/248.4 |
| 4,491,588 | 1/1985 | Rosenburg et al. | 424/273 R |
| 4,569,935 | 2/1986 | Rosenberg et al. | 514/252 |
| 4,657,925 | 4/1987 | Horn | 514/438 |
| 4,758,580 | 7/1988 | Numasaki et al. | 514/345 |
| 4,837,333 | 6/1989 | Manley et al. | 548/341 |
| 4,886,818 | 12/1989 | Numasaki et al. | 514/345 |
| 4,916,118 | 4/1990 | Fidler et al. | 514/16 |
| 4,942,162 | 7/1990 | Rosenburg et al. | 514/252 |
| 5,001,134 | 3/1991 | Ferrand et al. | |
| 5,023,090 | 6/1991 | Levin | 424/520 |
| 5,057,530 | 10/1991 | Barner et al. | 514/365 |
| 5,059,590 | 10/1991 | Ueda et al. | 514/23 |
| 5,132,315 | 7/1992 | Kohn et al. | 514/359 |
| 5,273,992 | 12/1993 | Brugnara et al. | 31/415 |
| 5,326,790 | 7/1994 | Thornfeldt | 514/784 |
| 5,358,959 | 10/1994 | Halperin et al. | 514/396 |
| 5,385,938 | 1/1995 | Yu et al. | 514/557 |
| 5,389,677 | 2/1995 | Yu et al. | 514/557 |

FOREIGN PATENT DOCUMENTS

| | | |
|---|---|---|
| 1004029 | 9/1990 | Belgium . |
| 2273873 | 12/1992 | United Kingdom . |
| WO91/19707 | 12/1991 | WIPO . |
| WO94/18967 | 9/1994 | WIPO . |
| WO94/18968 | 9/1994 | WIPO . |

OTHER PUBLICATIONS

Carter et al; Chemotherapy of Cancer, John Wiley & Sons, pp. 361–365. (1981).
Rosenberg, E.W. et al., Improvement of Psoriasis of the Scalp with Ketaconazole; Arch. Dermatol, Jun. 1982; 370–371.
Shelnitz, L.S. et al., Etretinate Therapy for Generalized Pustular Psoriasis in Children; Arch. Dermatol. Feb. 1987; pp. 230–233.
Lee, R.E. et al., Interleukin 2 and Psoriasis; Arch. Dermatol. V.124, Dec. 1988; pp. 1811–1815.
Going, S., The Treatment of Psoriasis; the Practitioner, Jul. 1988, v. 232; pp. 824–827.
Al–Ghamdi, F. et al., Dramatic Effect of Cyclosporin in Generalized Pustular Psoriasis–The Effective Dose; Saudi Med.J.v.13 No.5 (1991).
Dixon, B.S. et al., Histidine Regulation of Cyclic AMP Metabolism in Cutlured Renal Epithelial LLC–PK1 Cells; J. Biol. Chem., v. 265, No. 2, Jan. 15, 1990; pp. 760–766.
Fisher, J. et al., Therapeutic Failures with Miconazole; Antimicrobial Agents and Chemotherapy; Jun. 1978; pp. 965–968.
Coskey, R.J., Dermatologic Therapy; 1993; J. Of the American Academy of Dermatology; Nov. 1994, pp. 764–774.
Heel, R.C. et al., Miconazole; A Preliminary Review of its Therapeutic Efficacy in Systemic Fungal Infections, (1980), 7–30, Drugs 19.
Ritter, W. et al., Pharmacokinetic Fundamentals of Vaginal Treatment with Clotrimazole; (1982); 37–42; Chemotherapy 28.
Ritter, W.; Pharmacokinetic Fundamentals of Vaginal Treatment with Clotrimazole; Am J. Obstet. Gynecol., 152:945–947 (1985).
Duhm, B. et al., The Pharmacokinetics of Clotrimazole 14C; (Jul. 1974); 13–16; Postgraduate Medical Journal 50.
F. Delbarre, On the Possible Anti–Rheumatic Effects (Immuno–effector ?) of Imidazole Derivatives (levamisole, clortrimazole, niridazole), Biomedicine, 1977, 27, 97–98.
Knud Lund–Olesen, Clotrimzaole, Plasma Cortisol and Rheumatoid Arthritis; Current Therapeutic Research, vol. 21, No. 5, May, 1977 704–706.
W. Dennison et al., A Double Blind Placebo Controlled Trial of Low Dose Clotrimazole in Rheumatoid Arthritis; The Journal of Rheumatology, 1990; 17;8; 1003–1007.
Wojtulewski et al., Clotrimazole in rheumatoid Arthritis; Annals of the Rheumatic Diseases; 1980, 39, 469–572.
Carter et al. Chemotherapy of Cancer, Second Edition 361–365 (1982).

(List continued on next page.)

*Primary Examiner*—Theodore J. Criares
*Attorney, Agent, or Firm*—Edward R. Gates; Wolf, Greenfield & Sacks, P.C.

[57] ABSTRACT

The Applicant has identified a particular class of imidazoles that inhibit nonprostate cancer cell proliferation. These imidazoles can be used to beneficially treat a variety of cancers. The imidazoles can be administered in a variety of formulations, including long-term sustained release implants and anti-cancer cocktails.

26 Claims, 2 Drawing Sheets

OTHER PUBLICATIONS

Najid et al. Comparative Studies of Steroidogenesis inhibitors (econazole, ketoconazole) on human breast cancer MCF–7 cell . . . cytometric DNA analysis; Chemical Abstracts, vol. 106, 1987; 116:187584x.

Sawyer, P. et al., Clotrimazole; A Review of its Antifungal Activity and Therapeutic Efficacy; Drugs 9:424–447; (1975).

Ohnishi, S.T. et al., Inhibition of the In Vitro Formation of Dense Cells and of Irreversibly Sickled Cells by Charybdotoxin, A Specific Inhibitor of Calcium–Activated Potassium Efflux; 199–203; Biochemica et Biophysica Acta 1010 (1989).

Wolff, D. et al. Charybdotoxin Blocks with High Affinity the Ca–Activated K+ Channel of HB A and Hb S Red Cells; Individual Differences In the Number of Channels; J. Membrane Biol. 106.243-252 (1988).

Brugnara, C. et al., Ca2+–activated K+ Transport in Erythrocytes J. Biol. Chem.; 1993; 8760–8768.

De Franceschi, L.; Treatment with Oral Clotrimazole Blocks Ca2+–activated K+ Transport and Reverses Erythrocyte Dehydration in Transgenic SAD Mice; J. Clin. Invest. 93:1670–1676; Apr. 1994.

Brugnara, C. et al., Inhibition of Ca2+–dependent K+ Transport and Cell Dehydration in Sickle Erythrocytes by Clotrimazole and Other Imidazole Derivatives; J. Clin. Invest. 92:520–526; Jul. 1993.

Society of General Physiologists 48th Annual Symposium; Ion Channels and Genetic Diseases; Sep. 8, 1994.

Muhktar, H. et al., Clotrimazole, an Inhibitor of Epidermal Benzo(a)pyrene Metabolism and DNA Binding and Carcinogenicity of the Hydrocarbon; Cancer Res., 44:4283–4240, Oct. 1984.

Calmodulin Antagonists in Psoriasis; SCRIP No. 1797, Feb. 23, 1993 p. 23.

Fogue–Lafitte et al. Effects of ketoconazole on the proliferation; Cancer Cell Res. 52:6827–6831 (1992).

Tzanakakis et al., Inhibition of Hepatic Metastisis, Cancer, 65:446–451 (1990).

Nardone, et al., Ketoconazole; A Thromboxane Synthetase; J. Surgical Res., 44: 425–429 (1988).

Chemical Abstracts: CA 106: 209231c (1987).

Chemical Abstracts: CA 101:183620 (1984).

Chemical Abstracts: CA 116: 187584x (1992).

Marie Elisabeth Forgue–Lafitte, Anne–Marie Coudray, Dominique Fagot, and Jan Mester—"Effects of Ketoconazole on the Proliferation and Cell Cycle of Human Cancer Cell Lines", Cancer Research 52, 6827–6831, Dec. 15, 1992.

George N. Tzanakakis, MD., Kailash C. Agarwal, PhD., Michael P. Vezeridis, MD.—"Inhibition of Hepatic Metastasis From a Human Pancreatic Adenocarcinoma (RWP-2) in the Nude Mouse" by Prostacyclin, Forskolin, and Ketoconzzole, Cancer, vol. 65, Feb. 1, 1990.

Patricia A. Nardone, M.D., Gus J. Slotman, M.D., and Michael P. Vezeridis, M.D., "Ketoconazole: A Thromboxane Synthetase and 5–Lipoxygenase Inhibitor with Antimetastatic Activity in B16–F10 Melanoma", Journal of Surgical Research 44,425–429 (1988).

W. Wouters et al.; Effects of Liarozole, a New Antitumoral Compound, on Retinoic Acid–induced Inhibition of Cell Growth and on Retinoic Acid Metabolism in MCF–7 Human Breast Cancer Cells; May 15, 1992; pp. 2841–2846; Cancer Research 52.

A. Najid and M. Ratinaud; Comparative Studies of Steroidogenesis Inhibitors (Econazole, Ketoconazole) on Human Breast Cancer MCF–7 Cell Proliferation by Growth Experiments, Thymidine Incorporation and Flow Cytometric DNA Analysis; 1991; pp. 385–390; Tumori 77.

N. Burres et al.; Antitumor Activity and Biochemical Effects of Topsentin; 1991; pp. 745–751; Biochemical Pharmacology.

T. Nordstrom et al.; Mitosis–Arresting Effect of the Calcium Channel Inhibitor SK&F 96365 on Human Leukemia Cells; 1992; pp. 487–494; Experimental Cell Research.

A. Galeano et al.; Antitumor Activity of Some Ruthenium Derivatives in Human Colon Cancer Cell Lines in vitro; 1992; pp. 821–824; Drug Res.

CANCER TREATMENTS

FIELD OF THE INVENTION

The invention relates in general to the field of cancer and more particularly to the use of imidazoles that inhibit the $Ca^{++}$ activated potassium channel in arresting non-prostate cancer cell proliferation.

BACKGROUND OF THE INVENTION

It has been said that one-third of all people in the United States will develop cancer. Although remarkable progress has been made in understanding the biological basis of and in treating cancer, cancer remains second only to cardiac disease as the main cause of death in the United States.

Chemotherapy is an important tool in treating cancer. In 1945, there was but a single agent known to be an effective antineoplastic drug. Today, there are more than 50. Nevertheless, the search for effective antineoplastic drugs and drug combinations has, if anything, intensified in an effort to find even more effective agents for treating the myriad of cancers that threaten and take the lives of so many.

Imidazoles are synthetic antifungal agents that are used both topically and systemically. Indications for their use include ringworm, tinea versicolor and mucocutaneous candidiasis. These compounds are believed to act by inhibiting ergosterol synthesis in the fungal cell wall, and when given topically, may cause direct damage to the cytoplasmic membrane.

The fungi comprise five widely differing classes of primitive flora, and the variation in cell physiology and biochemistry are extreme. As a result, most antifungal agents have a very narrow spectrum of antifungal activity.

Various imidazoles have been suggested as treatments for prostate cancer. The only one known to the applicants to have been tested is ketoconazole. Ketoconazole is an antifungal agent that, in high doses, inhibits testicular and adrenal synthesis of steroid hormones, including testosterone. The ability of ketoconazole to block steroid synthesis has prompted its use in the treatment of advanced prostate carcinoma because prostate cancer cells are highly dependent upon testosterone. The major sites of action appear to be in the inhibition of 17-20 desmolase, partial blockade of 17-hydroxylase and marked inhibition of 21- and/or 11-hydroxylase, all major enzymes of the androgenic hormone synthetic pathways.

In the recent past, newer methods of androgen ablation for the treatment of metastatic prostate carcinoma have been developed as alternatives to the standard forms of therapy: oral estrogens and surgical castration. Luteinizing hormone-release hormone (LHRH) analogs, potent inhibitors of testosterone production, have recently emerged as major players in the long term treatment of advanced prostate cancer. In contrast, ketoconazole has been found to be excellent for short-term usage prior to bilateral orchiectomy and when prompt therapeutic response is needed but orchiectomy cannot be performed. In high doses, ketoconazole causes castrate levels of testosterone within 24 to 48 hours; therefore, it is extremely useful in the initial medical treatment of patients with metastatic prostate cancer who need a prompt therapeutic response. Thus, ketaconazole has been used as a hormonal adjuvant for prostate cancer treatment; it reduces plasma testosterone to castration levels. Ketoconazole, as will be described below, is not useful for inhibiting proliferation of the nonprostate cancer cells tested.

SUMMARY OF THE INVENTION

The Applicant has identified a particular class of imidazoles that inhibit nonprostate cancer cell proliferation. These imidazoles can be used to beneficially treat various cancers.

According to one aspect of the invention, a method for treating cancer is provided. An imidazole is administered to a subject that has a nonprostate cancer. The imidazole is an inhibitor of the $Ca^{++}$ activated potassium channel and is an inhibitor of nonprostate cancer cell proliferation. The methods are particularly useful in connection with the treatment of cancers that are nonhormone-sensitive. Preferred imidazoles are clotrimazole, miconazole and econazole.

According to another aspect of the invention, a method for inhibiting the growth of nonprostate cancer cells is provided. The cells of a species are contacted with an imidazole that inhibits the $Ca^{++}$ activated potassium channel of erythrocytes of the species. Such methods may be in vivo or ex vivo.

Preferrably, the cancer cells are in a preparation, tissue, subject or environment that is substantially free of fungi. As such, the treatment typically is for subjects that are otherwise free of indications for the preferred imidazoles.

According to another aspect of the invention, a sustained release implant containing an imidazole as described above is provided. The implant is constructed and arranged for the long-term delivery of the imidazole when implanted in vivo. Sill another aspect of the invention is a cocktail of anticancer agents, including an imidazole as described above.

DETAILED DESCRIPTION OF PREFERRED EMBODIMENTS

Figure 1:
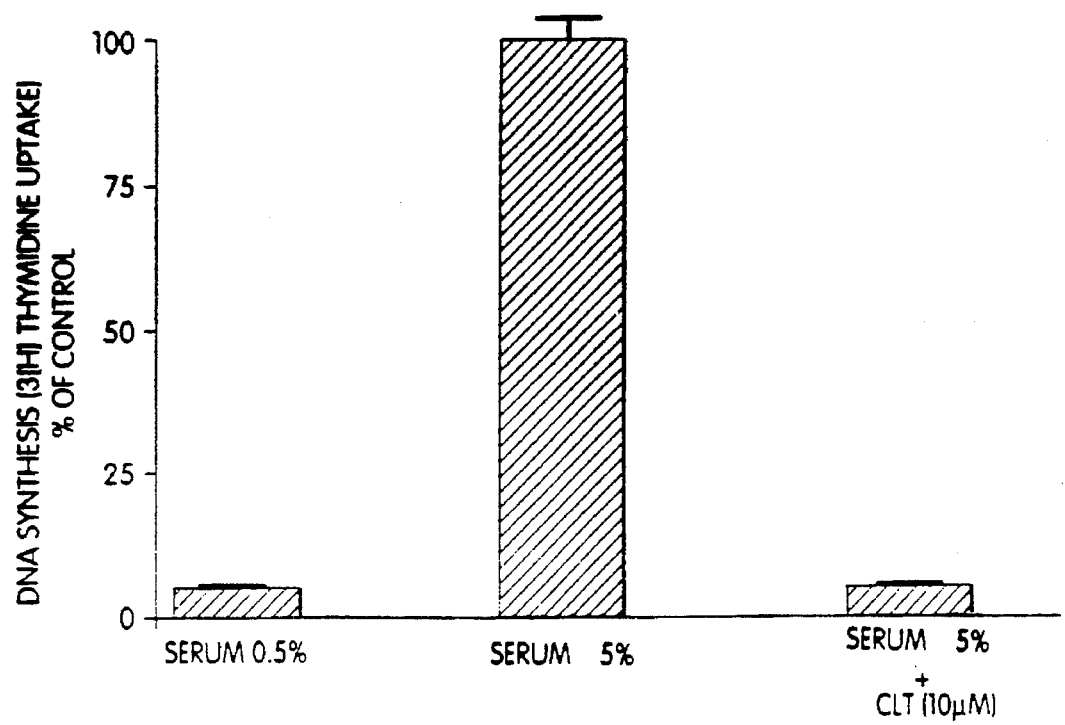
FIG. 1 is a graph illustrating the ability of clotrimazole to inhibit nonprostate cancer cell proliferation.

The invention is used in connection with treating non-prostate cancers. Nonprostate cancers include: biliary tract cancer; brain cancer, including glioblastomas and medelloblastomes; breast cancer; cervical cancer; choriocarcinoma; colon cancer; endometrial cancer; esophogeal cancer; gastric cancer; hematological neoplasms, including acute lymphocytic and myelogeneous leukemia, multiple myeloma, AIDS associates leukemias and adult T-cell leukemia lymphoma; intraepithelial neoplasms, including Bowen's disease and Paget's disease; liver cancer; lung cancer; lymphomas, including Hodgkin's disease and lymphozytic lymphomas; neuroblastomas; oral cancer, including squamous cell carcinoma; ovarian cancer, including those arising from epithelial cells, stromal cells, germ cells and mesenchymal cells; pancreas cancer; rectal cancer; sarcomas, including leiomyosarcoma, rhabdomyosarcoma, liposarcoma, fibrosarcoma and osteosarcoma; skin cancer, including melanoma, Kaposi's sarcoma, basocellular cancer and squamous cell cancer; testicular cancer, including germinal tumors (seminoma, non-seminoma (teratomas, choriocarcinomas)), stromal tumors and germ cell tumors; thyroid cancer, including thyroid adenocarcinoma and medullar carcinoma; and renal cancer including adenocarcinoma and Wilms tumor.

Proliferation of cancer cells is a main pathological feature of cancer. Proliferation of prostate cancer cells can be hormone (testosterone)-dependent; that is, proliferation of prostate cancer cells can be inhibited or arrested by eliminating the presence of testosterone, such as by castration. As discussed above, ketoconazole has been tested as an anticancer agent for prostate cancer because of its ability to block testosterone synthesis. Ketoconazole, on the other hand, was ineffective in inhibiting the growth of the non-prostate cancer cells tested by the applicants.

The imidazoles useful in this invention are believed to have a different mechanism of action and are useful in inhibiting and arresting the growth of cancer cells that do not depend upon the presence of hormones for proliferation or nonproliferation (i.e., nonhormone-dependent cancers.)

The compounds useful in the present invention are imidazoles that inhibit the $Ca^{++}$ activated potassium channel. Such imidazoles are either known to those of ordinary skill in the art or can be identified without undue experimentation using established tests routinely employed by those of ordinary skill in the art. One such test involves human erythrocytes and is described in the examples, below. When using this test, it is desirable to select imidazoles that are inhibitory to an extent of at least about 75%.

The imidazoles of the invention also inhibit nonprostate cancer cell proliferation. Inhibition of such proliferation may be tested without undue experimentation using established tests routinely employed be those of ordinary skill in the art (See e.g. examples below.) The imidazoles used in the methods of this invention preferably are inhibitory of nonprostate cancer cell proliferation in such tests to an extent of at least about 75%.

It was not expected that inhibitors of the $Ca^{++}$ activated potassium channel would inhibit nonprostate cancer cell proliferation. Other specific inhibitors of the $Ca^{++}$ activated potassium channel (such as charybdotoxin, caliotoxin and iberotoxin) do not inhibit proliferation of nonprostate cancer cells. Moreover, inhibitors of other transport systems that are activated by mitogens, such as ouabain (highly specific inhibitor of the Na/K pump) and amiloride (inhibitor of Na/H exchange) do not inhibit cell proliferation. Thus, the results obtained by the applicants are surprising.

Without limiting the invention to the use of the specific compounds listed, the following is a list of preferred compounds and well-characterized salts thereof useful in the methods of the invention.

Clotrimazole

1H-Imidazole, 1-[(2-chlorophenyl)diphenylmethyl]-, Lotrimin (Schering); Mycelex (Miles)

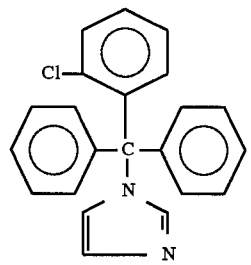

1-(o-Chloro-α,α-diphenylbenzyl)imidazole [23593-75-1]
$C_{22}H_{17}ClN_2(344.84)$.

Econazole

1H-Imidazole, (±)-1-[2-[(4-chlorophenyl)methoxy]-2-(2,4-dichlorophenyl)ethyl]-, mononitrate, Ecostatin (Squibb)

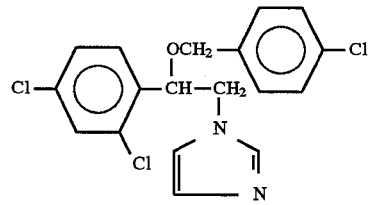

(±)-1-[2,4-Dichloro-β-[(p-chlorobenzyl)oxy]phenethyl]imidazole mononitrate [68797-31-9]$C_{18}H_{15}Cl_3N_2O$.

Econazole Nitrate

1H-Imidazole, (±)-1-[2-[(4-chlorophenyl)methoxy]-2-(2,4-dichlorophenyl)ethyl]-, mononitrate, Ecostatin (Squibb)

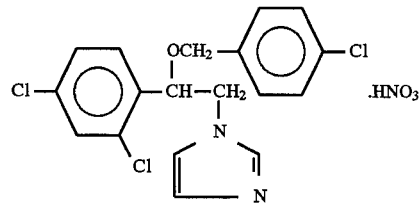

(±)-1-[2,4-Dichloro-β-[(p-chlorobenzyl)oxy]phenethyl]imidazole mononitrate [68797-31-9]$C_{18}H_{15}Cl_3N_2O.HNO_3(440.70)$.

Miconazole

1H-Imidazole, 1-[2-(2,4-dichlorophenyl)-2-[(2,4-dichlorophenyl)methoxy]ethyl]-, Monistat(Janssen)

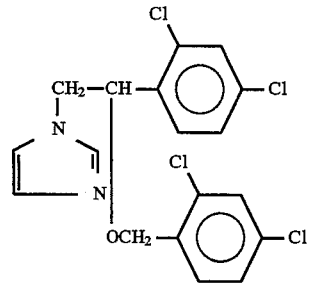

1-[2,4-Dichloro-β-[(2,4-dichlorobenzyl)oxy]phenethyl]imidazole [22916-47-8]$C_{18}H_{14}Cl_4N_2O(416.12)$.

Miconazole Nitrate

Monistat (Ortho)
[22832-87-7]$C_{18}H_{14}Cl_4N_2O.HNO_3(479.15)$.

The above imidazoles are well recognized, pharmacologically characterized, and licensed for use by the FDA today either as antimycotic agents or antiprotozoal agents. As such, established and empirically documented parameters regarding their limited toxicity and their useful dosages are well described in the scientific and medical literature.

The imidazoles used in the methods of the invention may be administered per se (neat) or in the form of a pharmaceutically acceptable salt. When used in medicine, the salts should be both pharmacologically and pharmaceutically acceptable, but non-pharmaceutically acceptable salts may conveniently be used to prepare the free active compound or pharmaceutically acceptable salts thereof. Pharmacologically and pharmaceutically acceptable salts include, but are not limited to, those prepared from the following acids: hydrochloric, hydrobromic, sulphuric, nitric, phosphoric, maleic, acetic, salicyclic, p-toluenesulfonic, tartaric, citric, methanesulphonic, formic, malonic, succinic, naphthalene-2-sulphonic, and benzenesulphonic. Also, pharmaceutically acceptable salts can be prepared as alkaline metal or alkaline earth salts, such as sodium, potassium or calcium salts of the carboxylic acid group. Thus, the present invention involves the use of pharmaceutical formulations which comprise certain imidazoles together with one or more pharmaceutically acceptable carriers and optionally other therapeutic ingredients. The carrier(s) and other ingredients of course must be pharmaceutically acceptable.

Analogs of the foregoing compounds that act as functional equivalents also are intended to be embraced as equivalents and within the scope of the invention.

A subject as used herein means: Humans, primates, horses, cows, pigs, sheep, goats, dogs, cats and rodents.

A variety of administration routes are available. The particular mode selected will depend, of course, upon the particular drug selected, the particular condition being treated and the dosage required for therapeutic efficacy. The methods of this invention, generally speaking, may be practiced using any mode of administration that is medically acceptable, meaning any mode that produces therapeutic levels of the imidazoles of the invention without causing clinically unacceptable adverse effects. Such modes of administration include oral, rectal, topical, nasal, transdermal or parenteral (e.g. subcutaneous, intramuscular and intravenous) routes. Transdermal or topical formulations may be particularly suitable, or even preferred, for certain cancers such as basal cell carcinoma and Kaposi's sarcoma. Formulations for oral administration include discrete units such as capsules, tablets, lozenges and the like. Other routes include intrathecal administration directly into spinal fluid and direct introduction onto, in the vicinity of or within cancer cells.

The compositions may conveniently be presented in unit dosage form and may be prepared by any of the methods well known in the art of pharmacy. Such methods include the step of bringing the active imidazole into association with a carrier which constitutes one or more accessory ingredients. In general, the compositions are prepared by uniformly and intimately bringing the imidazole into association with a liquid carrier, a finely divided solid carrier, or both, and then, if necessary, shaping the product.

Compositions of the present invention suitable for oral administration may be presented as discrete units such as capsules, cachets, tablets or lozenges, each containing a predetermined amount of the imidazole, in liposomes or as a suspension in an aqueous liquor or non-aqueous liquid such as a syrup, an elixir, or an emulsion.

Compositions suitable for parenteral administration conveniently comprise a sterile aqueous preparation of the imidazole, which is preferably isotonic with the blood of the recipient. This aqueous preparation may be formulated according to known methods using those suitable dispersing or wetting agents and suspending agents. The sterile injectable preparation may also be a sterile injectable solution or suspension in a non-toxic parenterally-acceptable diluent or solvent, for example as a solution in polythylene glycol and lactic acid. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectibles.

Other delivery systems can include sustained release delivery systems. Preferred sustained release delivery systems are those which can provide for release of the imidazoles of the invention in sustained release pellets or capsules. Many types of sustained release delivery systems are available. These include, but are not limited to: (a) erosional systems in which the imidazole is contained in a form within a matrix, found in U.S. Pat. Nos. 4,452,775 (Kent), 4,667,014 (Nestor et al.); and 4,748,024 and 5,239,660 (Leonard) and (b) diffusional systems in which an active component permeates at a controlled rate through a polymer, found in U.S. Pat. Nos. 3,832,252 (Higuchi et al.) and 3,854,480 (Zaffaroni). In addition, a pump-based hardware delivery system can be used, some of which are adapted for implantation.

Use of a long-term sustained release implant may be particularly suitable for treating certain cancers, including solid tumors. "Long term" release, as used herein, means that the implant is constructed and arranged to deliver therapeutic levels of the imidazole for at least 30, and preferably 60 days. Such implants can be particularly useful in treating solid tumors by placing the implant near or directly within the tumor, thereby affecting localized, high-doses of the imidazole. Such implants can be especially useful in delivering imidazoles that are not successfuly ingested, or that do not pass biological barriers, such as the blood/brain barrier. They also can be used to avoid undesirable canulation, such as when brain tumors are being treated. Long-term sustained release implants are well known to those of ordinary skill in the art and include some of the release systems described above.

Oral administration for many nonprostate cancers will be preferred because of the convenience to the patient, although topical and localized sustained delivery may be even more desirable for certain treatment regimens.

The imidazoles, when used in vivo, are administered in therapeutically effective amounts. A therapeutically effective amount means that amount necessary to inhibit the progression of or halt altogether progression of the particular nonprostate cancer being treated. Such amounts will depend, of course, on the particular condition being treated, the severity of the condition, and individual patient parameters including age, physical condition, size, weight and concurrent treatment. These factors are well known to those of ordinary skill in the art and can be addressed with no more than routine experimentation. It is preferred generally that a maximum dose be used, that is, the highest safe does according to sound medical judgment. It will be understood by those of ordinary skill in the art, however, that a patient may insist upon a lower dose or tolerable dose for medical reasons, psychological reasons or for virtually any other reasons.

Generally, daily oral doses of active compound will be from about 0.01 milligrams/kg per day to 1000 milligrams/kg per day. Small does (0.01–1 mg) may be administered initially, followed by increasing doses up to about 1000 mg/kg per day. In the event that the anti-cancer response in a subject is insufficient at such doses, even higher doses (or effective higher doses by a different, more localized delivery route) may be employed to the extent patient tolerance permits. Multiple doses per day are contemplated to achieve appropriate systemic levels of compounds.

The imidazoles useful in the invention may be delivered in the form of anti-cancer cocktails. An anti-cancer cocktail is a mixture of any one of the imidazoles useful with this invention with another anti-cancer drug and/or supplementary potentiating agent. The use of cocktails in the treatment of cancer is routine. In this embodiment, a common administration vehicle (e.g., pill, table, implant, injectable solution, etc.) would contain both the imidazole useful in this invention and the anti-cancer drug and/or supplementary potentiating agent.

Anti-cancer drugs are well known and include: Aminoglutethimide; Asparaginase; Bleomycin; Busulfan; Carboplatin; Carmustine (BCNU); Chlorambucil; Cisplatin (cis-DDP); Cyclophosphamide; Cytarabine HCI; Dacarbazine; Dactinomycin; Daunorubicin HCI; Doxorubicin HCI; Estramustine phosphate sodium; Etoposide (V16-213); Floxuridine; Fluorouracil (5-FU); Flutamide; Hydroxyurea (hydroxycarbamide); Ifosfamide; Interferon Alfa-2a, Alfa 2b; Leuprolide acetate (LHRH-releasing factor analogue); Lomustine (CCNU); Mechlorethamine HCI (nitrogen mustard); Melphalan; Mercaptopurine; Mesna; Methotrexate (MTX); Mitomycin; Mitotane (o. p'-DDD); Mitoxantrone HCI; Octreotide; Plicamycin; Procarbazine HCI; Streptozocin; Tamoxifen citrate; Thioguanine; Thiotepa; Vinblastine sulfate; Vincristine sulfate; Amsacrine (m-AMSA); Azacitidine; Hexamethylmelamine (HMM); Interleukin 2; Mitoguazone (methyl-GAG; methyl glyoxal bis-guanylhydrazone; MGBG); Pentostatin; Semustine (methyl-CCNU); Teniposide (VM-26) and Vindesine sulfate.

Supplementary potentiating agents likewise are well characterized and include: Tricyclic anti-depressant drugs (e.g., imipramine, desipramine, amitryptyline, clomipramine, trimipramine, doxepin, nortriptyline, protriptyline, amoxapine and maprotiline); non-tricyclic anti-depressant drugs (e.g., sertraline, trazodone and citalopram); $Ca^{++}$ antagonists (e.g., verapamil, nifedipine, nitrendipine and caroverine); Calmodulin inhibitors (e.g., prenylamine, trifluoroperazine and clomipramine); Amphotericin (e.g., Tween 80 and perhexiline maleate); Triparanol analogues (e.g., tamoxifen); antiarrhythmic drugs (e.g., quinidine); antihypertensive drugs (e.g., reserpine); and Thiol depleters (e.g., buthionine and sulfoximine).

The imidazoles of the invention, when used in cocktails, are administered in therapeutically effective amounts. A therapeutically effective amount will be determined by the parameters discussed above; but, in any event, is that amount which establishes a level of the drug in the area of the tumor which is effective in inhibiting the tumor growth.

EXAMPLES

Materials

Abbreviations: ChTX, Charybdotoxin; CLT, clotrimazole; ECZ, econazole; MCZ, miconazole; FCZ, fluconazole; METZ, metronidazole; IbTX, iberotoxin; KTX, kaliotoxin; DIDS, di-isothiocyano-disulfonyl stilbene; hemoglobin concentration; MCHC, mean corpuscular hemoglobin concentration; MOPS, 3-[N-morpholino]propanesulfonic acid.

Drugs and Chemicals

Synthetic charybdotoxin (ChTX) was purchased from Peptides International (Louisville, Ky.). A23187 was purchased from Calbiochem-Behring (LaJolla, Calif.). Fluconazole was provided by Pfizer Inc., Groton, Conn., disulfonic acid (MOPS), clotrimazole (CLT), miconazole, econazole, metronidazole, and all other drugs and chemicals were purchased from Sigma Chemical Co. (St. Louis, Mo.) and Fisher Scientific Co. (Fair Lawn, N.J.), and the radioisotope $^{86}Rb$ from Dupont (Billerica, Mass.)

Assays for Cell Proliferation

DNA synthesis assessed by the uptake of [3H]thymidine: Cells are grown in either 48 or 96 wells plates (Costar, Cambridge, Mass.) at $10^4$ and 0.8 $10^3$ cells per well, respectively, and grown in Dubelcco's modified Eagle's medium (DME, Gibco, Grand Island, N.Y.) supplemented with 10% heat-inactivated calf serum; they are kept at 37° C. in 5% $CO_2$. When they reach confluence, usually between 3 and 4 days, the medium is replaced with DME 0.5% serum to make them quiescent, and mitogenesis assays are performed 24 hours later.

Quiescent cells are exposed to a mitogenic stimulus, such as 10% serum, PDGF (Sigma Co. St. Louis, Mo.), bFGF (Upstate Biotechnologies, Lake Placid, N.Y.), or other appropriate mitogen according to the cell line, and 3 hours later 1 µCi/ml of [3H]thymidine (Dupont, Billerica, Mass.) is added to the wells, and the cells maintained at 37° C./5% CO2 for additional 21 hours. Then the cells are washed 3 times with DME medium and the acid-precipitable radioactivity is extracted with cold 10% TCA (Sigma, Co). After neutralization with 0.3N NaOH (Sigma Co.), aliquots are counted in a Packard Tri-Carb Scintillation counter (Packard Instrument, Downer's Grove, Ill.).

Measurement of cell density in culture plates: Cells of a specific test cell line are seeded at precisely the same low density in culture plates and incubated for approximately 12 hours in DME 10% serum, or other culture medium depending on the cell line tested. After 12 hours, the test drug, for example clotrimazole 10 µM, is added to the cell medium of one plate and a similar amount of only the carrier of the drug, for example ethanol 10 µl, to another plate. After 48 to 74 hours, the cell density in control (ethanol) and experimental (clotrimazole) plates is assessed under a light inverted microscope, by measuring the surface of the culture plate covered by the cell monolayer. Alternatively, the cells can be detached from the plate by incubation with trypsin (Sigma, Co.) 50% (v/v) in ethylene diaminotetraacetic acid (ECTA; Sigma, Co); then the cells are counted in an hemocytometer chamber (Fisher, Pittsburgh, Pa.).

Assays for Inhibitors of $Ca^{++}$ Activated K Channel $Ca^{++}$-sensitive K+ channels have wide distribution among cells, including the human red cell where they were originally discovered and which is the most commonly utilized assay system for activators and inhibitors of the channel for the following reasons: they are readily available, can be easily manipulated in the laboratory, and transport assays can be accurately standardized by reading the hemoglobin concentration of a red cell suspension.

Preparation of Human Red Blood Cells: Blood is collected in heparinized tubes and centrifuged in a Sorvall centrifuge (RB 5B, Du Pont Instruments, Newtown, Conn.) at 5° C. for 10 minutes at 3000 g. Plasma and buffy coat are carefully removed and the cells washed four times with a washing solution containing 150 mM choline chloride (Sigma Co), 1 mM MgC12 (Sigma Co), 10 mM Tris-MOPS (Sigma, Ca), pH 7.4 at 4° C.(CWS). An aliquot of cells is then suspended in an approximately equal volume of CWS, and from this original cell suspension hematocrit (Hct) and hemoglobin (optical density at 540 nm) are determined.

Methods to Test Inhibitors of the $Ca^{++}$ Activated K: To test inhibitors of the $Ca^{++}$ activated K channel, the channel is activated using the calcium ionophore A23187 (Chalbiochem).

By Atomic Absorption Spectrometry: Washed human erythrocyte are suspended at an hematocrit≈1% in CWS containing 0.150 mM CaCl2 (Sigma Co) Aliquots of 1 ml are removed at 0, 3 and 5 minutes, layered on top of 0.3 ml of the oil n-butyl phthalate (Fair Lane, N.J.) placed in an Eppendorf microtube (Fisher) and then centrifuged in a micro centrifuge for 20 seconds. At time 5.30 minutes, ionophore A23187 (1 μM final concentration) is added and samples removed and spin down through phthalate at times 6, 7, 8 and 9 minutes. The supernatant on top of the oil layer is removed and its K+ concentration is measured by atomic absorption spectrometry using a Perking Elmer model 5000 spectrometer (Perkin Elmer Corp., Norwolk, Conn.). The efflux of K+ (mmol/l cells/h) in the absence and presence of the inhibitor is calculated from the slope of the curves relating the K+ concentration in the supernatants (mmol/l cells) vs. time (min.).

By radioisotopic measurement of $^{86}$Rb influx. The incubation medium is the same but contains 2 mM KCl and 1 μCi/ml of the radioactive tracer $^{86}$Rb. After spinning the samples through the phthalate layer, the tubes are rapidly frozen (−80° C.) by immersion in methanol-dry ice, the tips of the tubes containing the packed red cells cut, and counted in a Packard Gamma Counter.

EXAMPLE 1

The inhibitory effect of clotrimazol (CLT) on cell proliferation was assessed in cancerous cells. Quiescent human colon adenocarcinoma and human lung adenocarcinoma cells were stimulated with 5% fetal calf serum and synthesis of DNA was assessed by the incorporation of [3H]thymidine measures 24 hours later. As shown in FIG. 1, 10 μM CLT completely inhibited DNA systhesis in both cancer cell lines. The effect was not due to a toxic, non-specific, effect because it was reversed by removing CLT and re-stimulating the cells with 5% fetal calf serum (FIG. 1).

EXAMPLE 2

Figure 2:
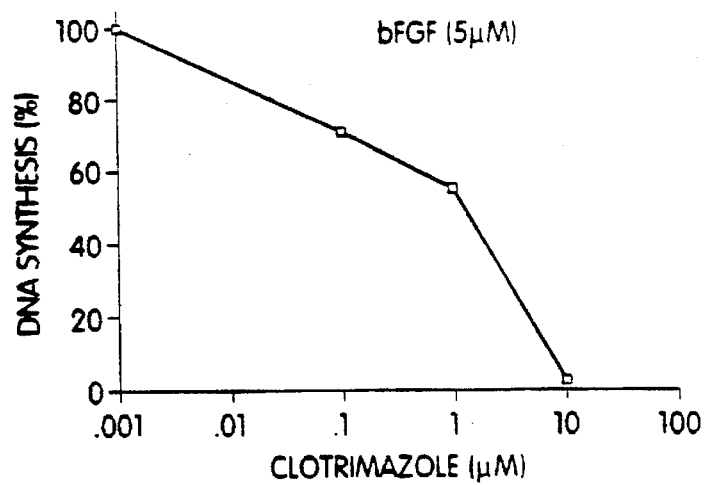
FIG. 2 is a graph showing that clotrimazole inhibits DNA synthesis in a dose-dependent fashion.

Dose response inhibitors of DNA synthesis by clotrimazole was tested using rat vascular smooth muscle cells as described above. Clotrimazole was tested at concentrations of 0.001 μM, 0.1 μM, 1 μM and 10 μM. Cells were stimulated using 5 μM bFGF. Inhibition was dose dependent, with 45% inhibition at 1 μM and complete inhibition at 10 μM. The $ID_{50}$ was about 1.5 μM. (FIG. 2)

EXAMPLE 3

Primary human sarcomas rabdomyosarcoma and liposarcoma: Fresh human cancer specimens were obtained from human subjects undergoing a surgical procedure; the tumors were treated with colagenase to dissociate the cells which were then seeded at low density ($1\times10^5$ in small culture chambers containing hybridomas grade culture medium supplemented with 5% fetal calf serum; after 12 hrs., when the cells were attached to the surface of the culture chambers, CLT (10 μM) or carrier (ethanol) were added *triplicate chambers). After 48 hours cell growth was assessed by optic miscroscopy calculating the surface of the culture flask covered by the cell monolayer. The growth of both sarcoma cells were completely arrested by CLT. More than 95% inhibition was obtained with 10 μM CLT.

EXAMPLE 4

Figure 3:
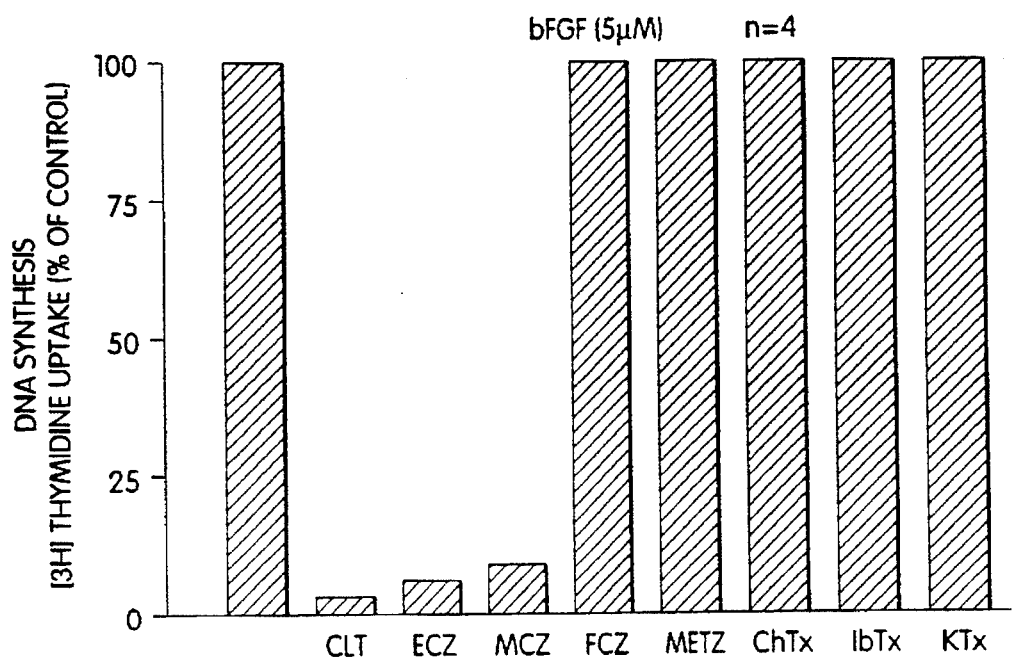
FIG. 3 is a graph comparing the effect upon cell-proliferation of a variety of drugs.

Other antimycotics were tested for their inhibition of bFGF-stimulated DNA synthesis in the primary human sarcoma cells of Example 3. As shown in FIG. 3, at a concentration of 10 μM, 3 compounds, CLT, econazole (ECZ) and miconazole (MCZ) inhibited DNA synthesis. The order of inhibitory potency was CLT more potent than ECZ, and ECZ more potent than MCZ. In contrast, other inhibitors of the $Ca^{++}$ activated K channel, namely Charybdotoxin, kaliotoxin and iberotoxin, also failed to inhibit DNA synthesis.

EXAMPLE 5

The inhibitory effect of (CLT) on the $Ca^{++}$ activated K channel of human erythrocytes was assessed in the presence of 60 μmol A23187/L cell and 100 μMCaCl$_2$. CLT markedly inhibited the $CA^{++}$ activated 86Rb influx and K efflux. Mean values of $ID_{50}$ (calculated with Dixon plot analysis) was 143±60 nM(n=3 ).

Figure 4:
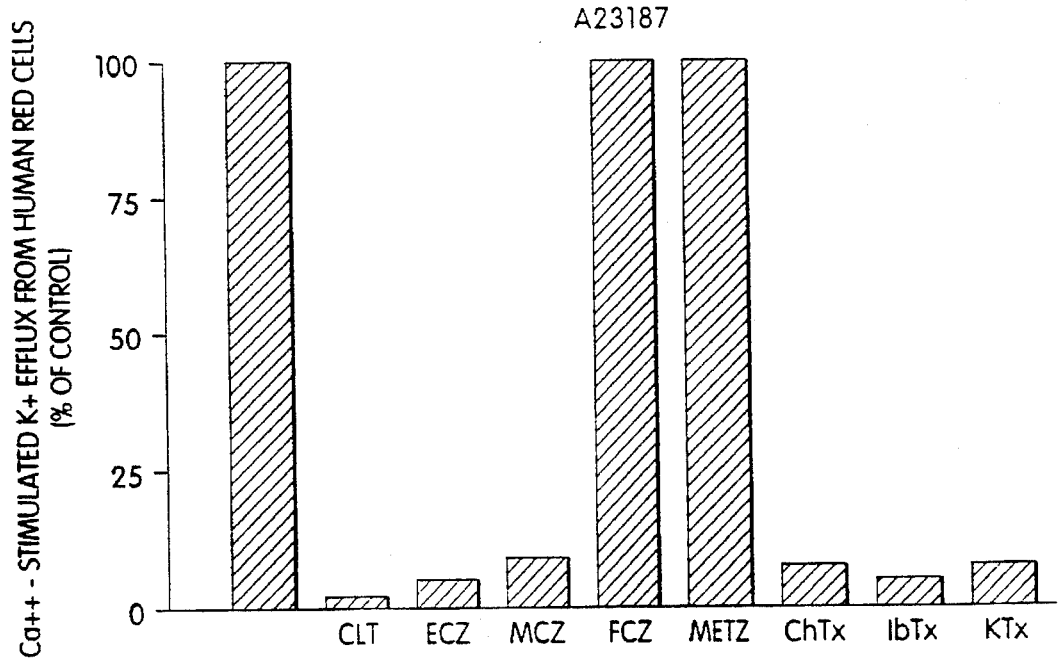
FIG. 4 is a graph comparing the effect upon the $Ca^{++}$ activated potassium channel of the same drugs tested in connection with FIG. 3.

Other antimycotics were tested for their inhibition of the Ca++ activated 86Rb influx human erythrocytes. The order of inhibitory potency was clotrimazole more than miconazole; and both of these were more than econazole. There was no inhibition by fluconazole, ornidazole and tinidazole, 2 related compounds, and only marginal with mitronidazole a member of the nitroimidazole group (FIG. 4).

EXAMPLE 6

Inhibition of tumor growth in vivo:

The efficacy of CLT was studied in inhibiting the growth of adenocarcinomas in rats. Animals were inoculated with LD100 doses of one tumor line and were randomly allocated to groups of five animals, which received in different doses of carrier alone or CLT (20, 50, 100 and 200 mg/kg) dissolved in peanut oil and administered by mouth with a special device adapted to a plastic catheter. Tumors were measured by size and weight on a daily basis, and growth rates were calculated. Nonparametric statistical comparisons were made among the median growth rates of all of the treatment groups. A significant reduction in median tumor growth rates was observed in animals treated with 100 and 200 mg/Kg of CLT.

Those skilled in the art will be able to ascertain with no more than routine experimentation numerous equivalents to the specific imidazoles and processes described herein. Such equivalents are considered to be within the scope of the invention and are intended to be embraced by the following claims in which

We claim:

1. A method for treating cancer sensitive to treatment with the compounds set forth herein comprising, administering to a subject that has a nonsteroid-hormone dependent cancer an effective amount of an imidazole selected from the group consisting of clotrimazole, miconazole and econazole.

2. A method for treating cancer as claimed in claim 1, wherein the imidazole is administered to a subject that has a cancer selected from the group consisting of:

biliary tract cancer; brain cancer; breast cancer; cervical cancer; choriocarcinoma; colon cancer; endometrial cancer; esophogeal cancer; gastric cancer; hematological neoplasms; intraepithelial neoplasms; liver cancer; lung cancer; lymphomas; neuroblastomas; oral cancer; ovarian cancer; pancreas cancer; rectal cancer; sarcomas; skin cancer; testicular cancer; thyroid cancer; and renal cancer.

3. A method for treating cancer as claimed in claim 1, wherein the imidazole is administered to a subject that has a cancer selected from the group consisting of:

biliary tract cancer; brain cancer; choriocarinoma; colon cancer; esophageal cancer; gastric cancer; hematological neoplasms; intraepithelial neoplasms; liver cancer; lung cancer; lymphomas; neuroblastomas; oral cancer; pancreas cancer; rectal cancer; sarcomas; skin cancer; thyroid cancer; and renal cancer.

4. A method for treating cancer as claimed in claim 1 wherein the imidazole is administered to a subject that has a cancer selected from the group consisting of lung cancer, melanoma, intraepithelial neoplasm, breast cancer, brain cancer, liver cancer and sarcomas.

5. A method for treating cancer as claimed in claim 1 wherein the imidazole is administered to a subject that has a cancer selected from the group consisting of lung cancer and melanoma.

6. A method for treating cancer as claimed in claim 1 wherein the imidazole is administered to a subject that has a cancer that is a lung cancer.

7. A method for treating cancer as claimed in claims 1, 2, 3, 4, 5 or 6 wherein the imidazole is clotrimazole.

8. A method for treating cancer as claimed in claim 4 wherein the imidazole is clotrimazole.

9. A method for treating cancer as claimed in claim 5 wherein the imidazole is clotrimazole.

10. A method for treating cancer as claimed in claim 6 wherein the imidazole is clotrimazole.

11. A method for treating cancer as claimed in claim 1 wherein the imidazole is administered to a subject that has a cancer selected from the group consisting of brain cancer, breast cancer, cervical cancer, choriocarcinoma, colon cancer, gastric cancer, hematological neoplasm, intraepithelial neoplasm, liver cancer, lung cancer, lymphoma, sarcoma, skin cancer, thyroid cancer and renal cancer.

12. A method for treating cancer as claimed in claim 11 wherein the imidazole administered to a subject that has a brain cancer.

13. A method for treating cancer as claimed in claim 11 wherein the imidazole is administered to a subject that has a breast cancer.

14. A method for treating cancer as claimed in claim 11 wherein the imidazole is administered to a subject that has a cervical cancer.

15. A method for treating cancer as claimed in claim 11 wherein the imidazole is administered to a subject that has a choriocarcinoma.

16. A method for treating cancer as claimed in claim 11 wherein the imidazole is administered to a subject that has a colon cancer.

17. A method for treating cancer as claimed in claim 11 wherein the imidazole is administered to a subject that has a gastric cancer.

18. A method for treating cancer as claimed in claim 11 wherein the imidazole is administered to a subject that has a hematological neoplasm.

19. A method for treating cancer as claimed in claim 11 wherein the imidazole is administered to a subject that has a intraepithelial neoplasm.

20. A method for treating cancer as claimed in claim 11 wherein the imidazole is administered to a subject that has a liver cancer.

21. A method for treating cancer as claimed in claim 11 wherein the imidazole is administered to a subject that has a lymphoma.

22. A method for treating cancer as claimed in claim 11 wherein the imidazole is administered to a subject that has a sarcoma.

23. A method for treating cancer as claimed in claim 11 wherein the imidazole is administered to a subject that has a skin cancer.

24. A method for treating cancer as claimed in claim 11 wherein the imidazole is administered to a subject that has a thyroid cancer.

25. A method for treating cancer as claimed in claim 11 wherein the imidazole is administered to a subject that has a renal cancer.

26. A method for treating cancer as claimed in claims 11, 12, 13, 14, 15, 16, 17, 18, 19, 20, 21, 22, 23, 24 or 25 wherein the imidazole is clotrimazole.

* * * * *